(12) United States Patent
Dhanak et al.

(10) Patent No.: US 7,019,008 B2
(45) Date of Patent: Mar. 28, 2006

(54) PYRROLIDINE SULFONAMIDES

(75) Inventors: Dashyant Dhanak, King of Prussia, PA (US); Steven D. Knight, King of Prussia, PA (US); Jian Jin, King of Prussia, PA (US); Ralph A. Rivero, King of Prussia, PA (US); Anthony Sapienza, West Chester, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 11/119,026

(22) Filed: Apr. 29, 2005

(65) Prior Publication Data

US 2005/0197345 A1    Sep. 8, 2005

Related U.S. Application Data

(63) Continuation of application No. 10/472,976, filed as application No. PCT/US02/09445 on Mar. 28, 2002, now abandoned.

(60) Provisional application No. 60/279,610, filed on Mar. 29, 2001, provisional application No. 60/279,592, filed on Mar. 29, 2001.

(51) Int. Cl.
*A61K 31/496* (2006.01)
*C07D 409/14* (2006.01)

(52) U.S. Cl. ............ 514/253.11; 514/218; 514/254.01; 540/575; 544/364; 544/372

(58) Field of Classification Search ............... 544/364, 544/372; 540/575; 514/218, 253.11, 254.01
See application file for complete search history.

(56) References Cited

U.S. PATENT DOCUMENTS 6,265,408 B1    7/2001   Forbes

OTHER PUBLICATIONS

Watson et al. Peptides, vol. 25, p. 1759-1766 (2004).*
Dhanak et al. Annual Reports in Medicinal Chemistry, vol. 38, p. 99-11-(2003).*

* cited by examiner

*Primary Examiner*—Emily Bernhardt
(74) *Attorney, Agent, or Firm*—Andrea V. Lockenour; Linda Hall; Edward R. Gimmi

(57) ABSTRACT

A compound of Formula (I):

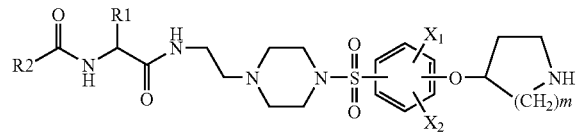

Formula (I)

wherein:
$R_1$ is $C_{1-6}$ alkyl, benzyl, or $(CH_2)_n$—$C(O)NH_2$; wherein the benzyl may be unsubstituted or substituted by one or two $C_{1-6}$ alkyl, halogen, $C_{1-6}$ alkoxy, or methylenedioxy groups;
$R_2$ is benzimidazolyl, quinolinyl, benzofuranyl, napthyl, indolyl, benzothiophenyl, phenyl, furanyl, thienyl, or pyridyl substituted or unsubstituted by one, two or three halogen, $C_{1-3}$ alkyl, $C_{1-3}$ alkoxy, or methylenedioxy groups;
$X_1$ and $X_2$ are independently hydrogen, halogen, $C_{1-3}$ alkyl, $C_{1-3}$ alkoxy, nitro, $CF_3$, or CN;
n is 1, 2, or 3;
m is 1, 2 or 3;
or a pharmaceutically acceptable salt thereof.

4 Claims, No Drawings

PYRROLIDINE SULFONAMIDES

This application is a continuation of Ser. No. 10/472,976 (now abandoned) which is a 371 of International Application No. PCT/US02/09445, filed 28 Mar. 2002; which claims the benefit of U.S. Provisional Application Nos. 60/279,610, filed 29 Mar. 2001 and 60/279,592, filed 29 Mar. 2001.

FIELD OF THE INVENTION

The present invention relates to pyrrolidine sulfonamides, pharmaceutical compositions containing them and their use as urotensin II antagonists

BACKGROUND OF THE INVENTION

The integrated control of cardiovascular homeostasis is achieved through a combination of both direct neuronal control and systemic neurohormonal activation. Although the resultant release of both contractile and relaxant factors is normally under stringent regulation, an aberration in this status quo can result in cardiohemodynamic dysfunction with pathological consequences.

The principal mammalian vasoactive factors that comprise this neurohumoral axis, namely angiotensin-II, endothelin-1, norepinephrine, all function via an interaction with specific G-protein coupled receptors (GPCR). Urotensin-II, represents a novel member of this neurohumoral axis.

In the fish, this peptide has significant hemodynamic and endocrine actions in diverse end-organ systems and tissues:
   smooth muscle contraction
      both vascular and non-vascular in origin including smooth muscle preparations from the gastrointestinal tract and genitourinary tract. Both pressor and depressor activity has been described upon systemic administration of exogenous peptide
   osmoregulation:
      effects which include the modulation of transepithelial ion ($Na^+$, $Cl^-$) transport. Although a diuretic effect has been described, such an effect is postulated to be secondary to direct renovascular effects (elevated GFR)
   metabolism:
      urotensin-II influences prolactin secretion and exhibits a lipolytic effect in fish (activating triacylglycerol lipase resulting in the mobilization of non-esterified free fatty acids)
      (Pearson, et. al. *Proc. Natl. Acad. Sci. (U.S.A.)* 1980, 77, 5021; Conlon, et. al. *J. Exp. Zool.* 1996, 275, 226.)
In studies with human Urotensin-II it was found that it:
   was an extremely potent and efficacious vasoconstrictor
   exhibited sustained contractile activity that was extremely resistant to wash out
   had detrimental effects on cardiac performance (myocardial contractility)

Human Urotensin-II was assessed for contractile activity in the rat-isolated aorta and was shown to be the most potent contractile agonist identified to date. Based on the in vitro pharmacology and in vivo hemodynamic profile of human Urotensin-II it plays a pathological role in cardiovascular diseases characterized by excessive or abnormal vasoconstriction and myocardial dysfunction. (Ames et. al. *Nature* 1999, 401, 282; Douglas & Ohlstein (2001). Trends Cardiovasc. Med., 10: in press). Compounds that antagonize the Urotensin-II receptor may be useful in the treatment of congestive heart failure, stroke, ischemic heart disease (angina, myocardial ischemia), cardiac arrhythmia, hypertension (essential and pulmonary), COPD, fibrosis (e.g. pulmonary fibrosis), restenosis, atherosclerosis, dyslipidemia, asthma, (Hay D W P, Luttmann M A, Douglas S A: 2000, Br J Pharmacol: 131; 10–12) neurogenic inflammation and metabolic vasculopathies all of which are characterized by abnormal vasoconstriction and/or myocardial dysfunction. Since U-II and GPR14 are both expressed within the mammalian CNS (Ames et. al. *Nature* 1999, 401, 282), they also may be useful in the treatment of addiction, schizophrenia, cognitive disorders/Alzheimers disease, (Gartlon J. Psychopharmacology (Berl) 2001 June; 155(4):426–33), impulsivity, anxiety, stress, depression, pain, migraine, and neuromuscular function. Functional U-II receptors are expressed in rhabdomyosarcomas cell lines and therefore may have oncological indications. Urotensin may also be implicated in various metabolic diseases such as diabetes (Ames et. al. *Nature* 1999, 401, 282, Nothacker et al., *Nature Cell Biology* 1: 383–385, 1999) and in various gastrointestinal disorders, bone, cartilage, and joint disorders (e.g. arthritis and osteoporosis); and genito-urinary disorders. Therefore, these compounds may be useful for the prevention (treatment) of gastric reflux, gastric motility and ulcers, arthritis, osteoporosis and urinary incontinence.

SUMMARY OF THE INVENTION

In one aspect this invention provides for pyrrolidine sulfonamides and pharmaceutical compositions containing them.

In a second aspect, this invention provides for the use of pyrrolidine sulfonamides as antagonists of urotensin II, and as inhibitors of urotensin II.

In another aspect, this invention provides for the use of pyrrolidine sulfonamides for treating conditions associated with urotensin II imbalance.

In yet another aspect, this invention provides for the use of pyrrolidine sulfonamides for the treatment of congestive heart failure, stroke, ischemic heart disease (angina, myocardial ischemia), cardiac arrhythmia, hypertension (essential and pulmonary), COPD, restenosis, asthma, neurogenic inflammation, migraine, metabolic vasculopathies, bone/cartilage/joint diseases, arthritis and other inflammatory diseases, fibrosis (e.g. pulmonary fibrosis), sepsis, atherosclerosis, dyslipidemia, addiction, schizophrenia, cognitive disorders/Alzheimers disease, impulsivity, anxiety, stress, depression, pain, neuromuscular function, diabetes, gastric reflux, gastric motility disorders, ulcers and genitourinary diseases.

The urotensin antagonist may be administered alone or in conjunction with one or more other therapeutic agents, said agents being selected from the group consisting of endothelin receptor antagonists, angiotensin converting enzyme (ACE) inhibitors, A-II receptor antagonists, vasopeptidase inhibitors, diuretics, digoxin, and dual non-selective $\beta$-adrenoceptor and $\alpha_1$-adrenoceptor antagonists.

Other aspects and advantages of the present invention are described further in the following detailed description of the preferred embodiments thereof.

DETAILED DESCRIPTION OF THE INVENTION

The present invention provides for compounds of Formula (I):

Formula (I)

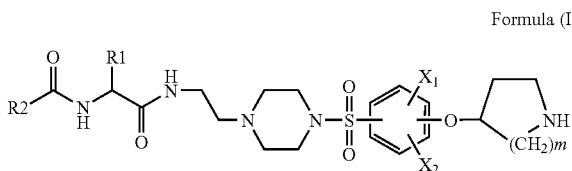

wherein:
R$_2$ is benzimidazolyl, quinolinyl, benzofuranyl, napthyl, indolyl, or benzothiophenyl, phenyl, furanyl, thienyl, or pyridyl substituted or unsubstituted by one, two or three halogen, C$_{1-3}$ alkyl, C$_{1-3}$ alkoxy, or methylenedioxy groups;
R$_1$ is C$_{1-6}$ alkyl, benzyl, or (CH$_2$)$_n$—C(O)NH$_2$; wherein the benzyl may be unsubstituted or substituted by one or two C$_{1-6}$ alkyl, halogen, C$_{1-6}$ alkoxy, or methylenedioxy groups;
X$_1$ and X$_2$ are independently hydrogen, halogen, C$_{1-3}$ alkyl, C$_{1-3}$ alkoxy, nitro, CF$_3$, or CN;
n is 1, 2, or 3;
m is 1, 2 or 3;
or a pharmaceutically acceptable salt thereof.

When used herein, the term "alkyl" includes all straight chain and branched isomers. Representative examples thereof include methyl, ethyl, n-propyl, iso-propyl, n-butyl, sec-butyl, iso-butyl, t-butyl, n-pentyl and n-hexyl.

When used herein, the terms 'halogen' and 'halo' include fluorine, chlorine, bromine and iodine and fluoro, chloro, bromo and iodo, respectively.

The compounds of the present invention may contain one or more asymmetric carbon atoms and may exist in racemic and optically active form. All of these compounds and their diastereoisomers are contemplated to be within the scope of the present invention.

Preferrably:
m is 1 or 2;
R$_1$ is isobutyl;
R$_2$ is benzothiopheneyl;
X$_1$ is hydrogen, 3-Bromo, or 3-Chloro; and
X$_2$ is hydrogen or 5-Chloro.

Preferred Compounds are:
Benzo[b]thiophene-2-carboxylic acid [(S)-1-(2-{4-[3-chloro-4-(piperidin-4-yloxy)-benzenesulfonyl]-piperazin-1-yl}-ethylcarbamoyl)-3-methyl-butyl]-amide
Benzo[b]thiophene-2-carboxylic acid [(S)-1-(2-{4-[3-bromo-4-(piperidin-4-yloxy)-benzenesulfonyl]-piperazin-1-yl}-ethylcarbamoyl)-3-methyl-butyl]-amide
Benzo[b]thiophene-2-carboxylic acid [(S)-1-(2-{4-[3-chloro-4-((S)-pyrrolidin-3-yloxy)-benzenesulfonyl]-piperazin-1-yl}-ethylcarbamoyl)-3-methyl-butyl]-amide
Benzo[b]thiophene-2-carboxylic acid [(S)-1-(2-{4-[3-bromo-4-((S)-pyrrolidin-3-yloxy)-benzenesulfonyl]-piperazin-1-yl}-ethylcarbamoyl)-3-methyl-butyl]-amide
Benzo[b]thiophene-2-carboxylic acid [(S)-3-methyl-1-(2-{4-[4-(piperidin-4-yloxy)-benzenesulfonyl]-piperazin-1-yl}-ethylcarbamoyl)-butyl]-amide
Benzo[b]thiophene-2-carboxylic acid [(S)-1-(2-{4-[3,5-dichloro-4-(piperidin-4-yloxy)-benzenesulfonyl]-piperazin-1-yl}-ethylcarbamoyl)-3-methyl-butyl]-amide Compounds of Formula (I) may be prepared as set forth in scheme 1.

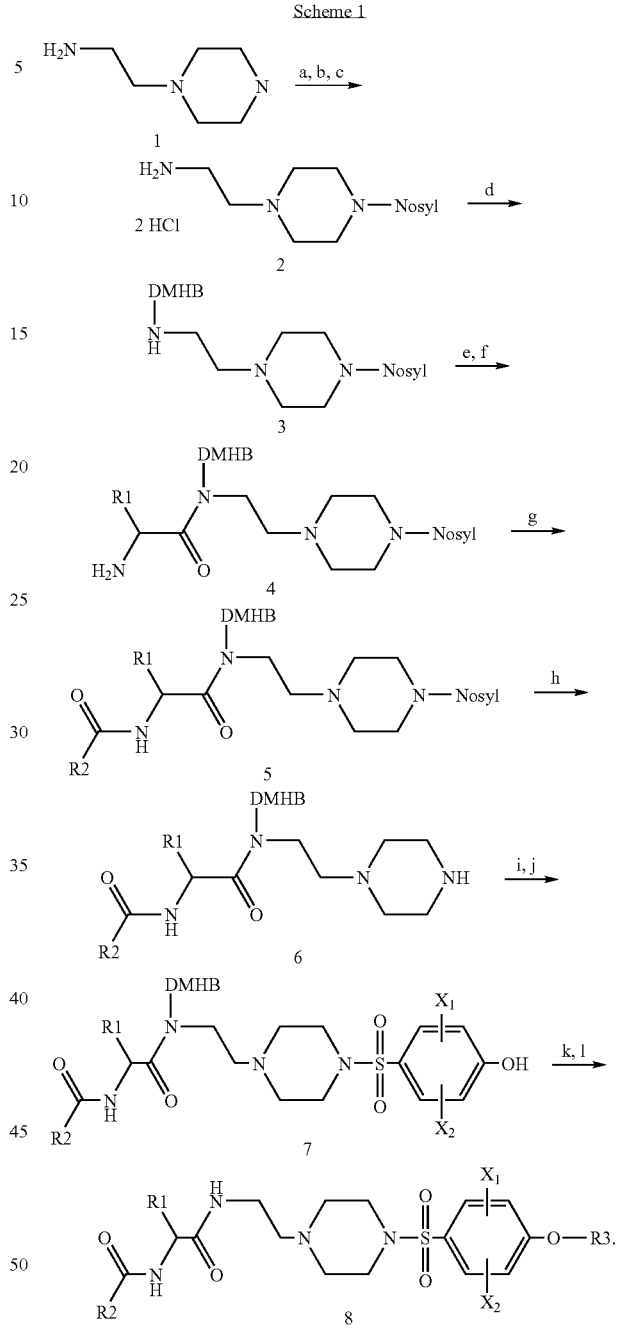

Scheme 1

Conditions: a) tert-butylchlorodiphenyl silane, triethylamine, CH$_2$Cl$_2$, 50° C.; b) 2-nitrobenzenesulfonyl chloride, 0° C.-rt; c) 4 M HCl in 1,4-dioxane, rt; d) 2,6-dimethoxy-4-polystyrenebenzyloxy-benzaldehyde (DMHB resin), Na(OAc)$_3$BH, diisopropylethylamine, 1% acetic acid in 1-methyl-2-pyrrolidinone, rt; e) Fmoc-HNCH(R$_1$)COOH, 1,3-diisopropylcarbodiimide, 1-hydroxy-7-azabenzotriazole, 1-methyl-2-pyrrolidinone, rt; f) 20% piperidine in 1-methyl-2-pyrrolidinone, rt; g) R$_2$COOH, 1,3-diisopropylcarbodiimide, 1-hydroxy-7-azabenzotriazole, 1-methyl-2-pyrrolidinone, rt; h) K$_2$CO$_3$, PhSH, 1-methyl-2-pyrrolidinone, rt; i) (X$_1$)(X$_2$)-4-hydroxy-benzenesulfonyl chloride, 1,2-dichloroethane, 1-methyl-2-pyrrolidinone, rt;

j) potassium trimethylsilanolate, tetrahydrofuran, rt; k) $R_2OH$, diisopropyl azodicarboxylate, $PPh_3$, tetrahydrofuran, −78° C.-rt; l) 50% trifluoroacetic acid in 1,2-dichloroethane, rt.

As shown in scheme 1, resin-bound amine 3 was prepared by reductive amination of 2,6-dimethoxy-4-polystyrenebenzyloxy-benzaldehyde (DMHB resin) piperazinyl-ethylamine HCl salt 2 which was prepared from 1-(2-aminoethyl)piperazine (1). Reactions of resin-bound amine 3 with various amino acids, followed by removal of the protecting group, resulted in the corresponding resin-bound amines 4. Amines 4 were then reacted with various acids to afford the corresponding resin-bound amides 5. Resin-bound amides 5 were subsequently treated with potassium carbonate and thiophenol to give secondary amines 6. Sulfonylation of resin-bound amines 6 with various hydroxy-benzenesulfonyl chlorides, followed by treatment with potassium trimethylsilanolate, produced resin-bound phenols 7. Phenols 7 were then reacted with various alcohols in the presence of triphenylphosphine and diisopropyl azodicarboxylate to give the corresponding resin-bound phenol ethers which were treated with 50% trifluoroacetic acid in 1,2-dichloroethane to afford targeted compounds 8.

With appropriate manipulation, including the use of alternative nitrogen protecting group(s), the synthesis of the remaining compounds of Formula (I) was accomplished by methods analogous to those above and to those described in the Experimental section.

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Ka to 40 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

These sulphonamide analogs may be used for the treatment of congestive heart failure, stroke, ischemic heart disease (angina, myocardial ischemia), cardiac arrhythmia, hypertension (essential and pulmonary), COPD, restenosis, asthma, neurogenic inflammation and metabolic vasculopathies, addiction, schizophrenia, impulsivity, anxiety, stress, depression, neuromuscular function, and diabetes.

The urotensin antagonist may be administered alone or in conjunction with one or more other therapeutic agents, said agents being selected from the group consisting of endothelin receptor antagonists, angiotensin converting enzyme (ACE) inhibitors, vasopeptidase inhibitors, diuretics, digoxin, and dual non-selective β-adrenoceptor and $α_1$-adrenoceptor antagonists.

No unacceptable toxicological effects are expected when compounds of the invention are administered in accordance with the present invention.

The biological activity of the compounds of Formula (I) are demonstrated by the following tests:

Radioligand Binding:

HEK-293 cell membranes containing stable cloned human and rat GPR-14 (20 ug/assay) were incubated with 200 pM [125I] h-U-II (200 $Ci/mmol^{-1}$ in the presence of increasing concentrations of test compounds in DMSO (0.1 nM to 10 uM), in a final incubation volume of 200 ul (20 mM Tris-HCl, 5 mM MgCl2). Incubation was done for 30 minutes at room temperature followed by filtration GF/B filters with Brandel cell harvester. $^{125}I$ labeled U-II binding was quantitated by gamma counting. Nonspecific binding was defined by $^{125}I$ U-II binding in the presence of 100 nM of unlabeled human U-II. Analysis of the data was performed by nonlinear least square fitting.

Ca²⁺-mobilization:

A microtitre plate based $Ca^{2+}$-mobilization FLIPR assay (Molecular Devices, Sunnyvale, Calif.) was used for the functional identification of the ligand activating HEK-293 cells expressing (stable) recombinant GPR-14. The day following transfection, cells were plated in a poly-D-lysine coated 96 well black/clear plates. After 18–24 hours the media was aspirated and Fluo 3AM-loaded cells were exposed to various concentrations (10 nM to 30 uM) of test compounds followed by h-U-II. After initiation of the assay, fluorescence was read every second for one minute and then every 3 seconds for the following one minute. The inhibitory concentration at 50% (IC50) was calculated for various test compounds.

Inositol Phosphates Assays:

HEK-2993-GPR14 cells in T150 flask were prelabeled overnight with 1 uCi myo-[$^3$H] inositol per ml of inositol free Dulbecco's modified Eagel's medium. After labeling, the cells were washed twice with Dulbecco's phosphate-buffered saline (DPBS) and then incubated in DPBS containing 10 mM LiCl for 10 min at 37° C. The experiment was initiated by the addition of increasing concentrations of h-U-II (1 pM to 1 μM) in the absence and presence of three different concentrations (0.3, 1 and 10 uM) of test compounds and the incubation continued for an additional 5 min at 37° C. after which the reaction was terminated by the addition of 10% (final concentration) trichloroacetic acid and centrifugation. The supernatants were neutralized with 100 ul of 1M Trizma base and the inositol phosphates were separated on AG 1-X8 columns (0.8 ml packed, 100–200 mesh) in formate phase. Inositol monophosphate was eluted with 8 ml of 200 mM ammonium formate. Combined inositol di and tris phosphate was eluted with 4 ml of 1M ammonium formate/0.1 M formic acid. Eluted fractions were counted in beta scintillation counter. Based on shift from the control curve $K_B$ was calculated.

Activity for the compounds of this invention range from (radioligand binding assay): Ki=5 nM–10000 nM (example 5 Ki=1400 nM).

The following Examples are illustrative but not limiting embodiments of the present invention.

EXAMPLE I

Preparation of Benzo[b]thiophene-2-carboxylic acid [(S)-3-methyl-1-(2-{4-[4-(piperidin-4-yloxy)-benzenesulfonyl]-piperazin-1-yl}-1-ethylcarbamoyl)-butyl]-amide a) 2-[4-(2-Nitro-benzenesulfonyl)-piperazin-1-yl]-ethylamine HCl salt To a solution of 100 mL (760.8 mmol) of 1-(2-aminoethyl)piperazine in 636 mL (4.56 mol) of triethylamine and 800 mL of anhydrous $CH_2CL_2$ at rt under argon was added 198 mL (760.8 mmol) of tert-butylchlorodiphenyl silane. The mixture was refluxed at 50° C. for 2.5 h. The mixture was then cooled to 0° C. 168.6 g (760.8 mmol) of 2-nitrobenzenesulfonyl chloride was added to the mixture in 3 portions. The resulting mixture was stirred at 0° C. for 1 h and warmed to rt and stirred at rt for 16 h. The mixture was diluted with 1.5 L of $CH_2Cl_2$ and poured into 1 L of 1 M $NaHCO_3$ aqueous solution. After stirring for 15 min, the organic layer was separated and washed with 1 L of 1 M $NaHCO_3$ aqueous solution. The resulting organic layer was dried over $K_2CO_3$ and concentrated in vacuo. The residue was dissolved into 400 mL of 1,4-dioxane. The solution was concentrated in vacuo to remove the remaining triethylamine.

The above residue was dissolved in 1 L of anhydrous 1,4-dioxane and was diluted with 2 L of anhydrous ether. The resulting mixture was treated with 800 mL of 4 M HCl solution in 1,4-dioxane under argon. The mixture was vigorously stirred at rt under argon for 1 h. The resulting suspension was filtered. The precipitation was washed 5 times with 500 mL portions of anhydrous ether. The resulting solid was dried in vacuum oven for 24 h to yield 2-[4-(2-nitro-benzenesulfonyl)-piperazin-1-yl]-ethylamine HCl salt as a white solid (340 g, 80% pure): MS (ESI) 315 [M+H]⁺ (which was contaminated with ~20% of the dinosyl-protected amine HCl salt: MS (ESI) 500 [M+H]⁺. It is not necessary to purify the crude product, however, the pure amine HCl salt example 1a could be obtained via recrystallization of the crude product in MeOH).

b) 4-Hydroxybenzenesulfonyl chloride

To chlorosulfonic acid (248 mL, 3.37 mol) cooled to –3° C. was added dropwise a solution of phenol (70 g, 0.744 mot) in 250 mL of anhydrous methylene chloride over a period of 1 hour under argon gas. The mixture was warmed to rt over 1 h and was stirred at rt for 1.5 h. The mixture was poured over ice, stirred for 30 min, and was extracted with methylene chloride (4×2 L). The resulting organic layer was dried over $MgSO_4$ and concentrated in vacuo to yield 4-hydroxybenzenesulfonyl chloride as a sticky brown solid (41.49 g, 29%): $^1$H NMR (400 MHz, $d_6$-DMSO) δ 7.29–7.38 (d, 2 H), 6.58–6.69 (d, 2 H).

c) Benzo[b]thiophene-2-carboxylic acid [(S)-3-methyl-1-(2-{4-[4-(piperidin-4-yloxy)-benzenesulfonyl]-piperazin-1-yl}-ethylcarbamoyl)-butyl]-amide To a mixture of 20.20 g (29.08 mmol, 1.44 mmol/g) of 2,6-dimethoxy-4-polystyrenebenzyloxy-benzaldehyde (DMHB resin) in 439.4 mL of 1% acetic acid in anhydrous 1-methyl-2-pyrrolidinone was added 27.42 a (70.8 mmol) of 2-[4-(2-nitro-benzenesulfonyl)-piperazin-1-yl]-ethylamine HCl salt and 25.33 mL (145.4 mmol) of diisopropylethyl amine, followed by addition of 30.8 g (145.4 mmol) of sodium triacetoxyborohydride. After the resulting mixture was shaken at rt for 65 h under argon gas, the resin was washed with $CH_2Cl_2$/methanol (1:1, 3×400 mL), DMF (3×400 mL), $CH_2Cl_2$ (1×400 mL) and methanol (2×400 mL). The resulting resin was dried in vacuum oven at 35° C. for 24 h. Elemental analysis N: 4.27, S: 5.25.

To a mixture of 10 g (7.914 mmol, 0.7914 mmol/g) of the above resin in 165 mL of anhydrous 1-methyl-2-pyrrolidinone was added 13.985 g (39.57 mmol) of Fmoc-Leu-OH and 1.077 g (7.914 mmol) of 1-hydroxy-7-azabenzotriazole, followed by addition of 7.490 mL (47.48 mmol) of 1,3-diisopropylcarbodiimide. After the resulting mixture was shaken at rt for 44 h, the resin was washed with 1-methyl-2-pyrrolidinone (3×150 mL), dichloroethane/methanol (1:1, 3×150 mL) and methanol (3×150 mL). The resulting resin was dried in vacuum oven at 35° C. for 24 h. An analytical amount of resin was cleaved with 50% trifluoroacetic acid in dichloroethane for 2 h at rt. The resulting solution was concentrated in vacuo: MS (ESI) 621 [M+H]⁺.

The above resin (7.914 mmol) was treated with 175 mL of 20% piperidine in anhydrous 1-methyl-2-pyrrolidinone solution. After the mixture was shaken at rt for 15 min, the solution was drained and another 175 mL of 20% piperidine in anhydrous 1-methyl-2-pyrrolidinone solution was added. The mixture was shaken at rt for another 15 min. The solution was drained and the resin was washed with 1-methyl-2-pyrrolidinone (3×175 mL), CH$_2$Cl$_2$/MeOH (1:1, 3×175 mL) and CH$_2$Cl$_2$ (3×175 mL). The resulting, resin was dried in vacuum oven at 35° C. for 24 h. An analytical amount of resin was cleaved with 50% trifluoroacetic acid in dichloroethane for 2 h at rt. The resulting solution was concentrated in vacuo: MS (ESI) 399 [M+H]$^+$.

To a mixture of 200 mg (0.1453 mmol, 0.7264 mmol/g) of the above dry resin in 5 mL of anhydrous 1-methyl-2-pyrrolidinone was added 129.5 mg (0.7265 mmol) of benzo[b]thiophene-2-carboxylic acid and 19.8 mg (0.1453 mmol) of 1-hydroxy-7-azabenzotriazole, followed by addition of 0.137 mL (0.8718 mmol) of 1,3-diisopropylcarbodiimide. After the resulting mixture was shaken at it for 48 h, the resin was washed with 1-methyl-2-pyrrolidinone (3×10 mL), CH$_2$Cl$_2$/MeOH (1:1, 3×10 mL) and CH$_2$Cl$_2$ (3×10 mL). The resulting resin was dried in vacuum oven at 35° C. for 24 h. An analytical amount of resin was cleaved with 50% trifluoroacetic acid in dichloroethane for 2 h at rt. The resulting, solution was concentrated in vacuo: MS (ESI) 559 [M+H]$^+$.

To a mixture of 0.1453 mmol of the above dry resin in 6 mL of 1-methyl-2-pyrrolidinone was added 200.8 mg (1.453 mmol) of K$_2$CO$_3$ and 0.0746 mL (0.7265 mmol) of PhSH. After the resulting mixture was shaken at rt for 20 h, the resin was washed with methanol (1×10 mL), H$_2$O (3×10 mL), methanol (1×10 mL), 1-methyl-2-pyrrolidinone (1×10 mL), CH$_2$Cl$_2$/methanol (1:1, 3×10 mL) and methanol (3×10 mL). The resulting resin was dried in vacuum oven at 35° C. for 24 h. An analytical amount of resin was cleaved with 50% trifluoroacetic acid in dichloroethane for 2 h at rt. The resulting solution was concentrated in vacuo: MS (EST) 747 [2M+H]$^+$, 374 [M+H]$^+$.

To a mixture of 0.1453 mmol of the above dry resin in anhydrous dichloroethane/1-methyl-2-pyrrolidinone solution (1:1, 7.5 mL) was added 0.2264 mL (2.799 mmol) of pyridine followed by the slow addition of 0.5393 g (2.799 mmol) of 4-hydroxybenzenesulfonyl chloride. After the resulting mixture was shaken at rt for 96 h, the resin was washed with 1-methyl-2-pyrrolidinone (3×10 mL), dichloroethane/methanol (1:1, 3×10 mL), dichloroethane (3×10 mL), methanol (1×10 mL), and dichloroethane (2×10 mL). The resulting resin was dried in vacuum oven at 35° C. for 24 h. To a mixture of the dry resin in anhydrous tetrahydrofuran (9.38 mL) was added 0.4713 g (3.674 mmol) of potassium trimethyl silanolate. After the reaction mixture was shaken for 23 h, the resin was washed with tetrahydrofuran (3×10 mL), 1-methyl-2-pyrrolidinone (2×10 mL), tetrahydrofuran (3×10 mL), dichloroethane/methanol (5×10 mL), and dichloroethane (3×10 mL). An analytical amount of resin was cleaved with 50% trifluoroacetic acid in dichloroethane for 2 h at rt. The resulting solution was concentrated in vacuo: MS (ESI) 530 [M+H]$^+$.

To a mixture of 200 mg of the above dry resin in 8.75 mL of anhydrous tetrahydrofuran was added 443 mg (2.199 mmol) of 4-Hydroxypiperidine-1-carboxylic acid tert-butyl ester and 577 mg (2.199 mmol) of triphenylphosphine. After the mixture was cooled to −70° C., 433 µL (2.199 mmol) of diisopropyl azodicarboxylate was added to the cold mixture. The resulting mixture was kept at −70° C. for 30 min while shaking. The mixture was then allowed to warm to 0° C. over 1 h and shaken at rt for 19 h. The resin was washed with tetrahydrofuran (3×10 mL), CH$_2$Cl$_2$/methanol (1:1, 10×10 mL). The resulting resin was dried in vacuum oven at 35° C. for 24 h. The dry resin was treated with 4 mL of 50% trifluoroacetic acid in dichloroethane at rt for 2 h. After the cleavage solution was collected, the resin was treated with another 4 mL of 50% trifluoroacetic acid in dichloroethane at rt for 10 min. The combined cleavage solutions were concentrated in vacuo. The residue was purified using a Gilson semi-preparative HPLC system with a YMC ODS-A (C-18) column 50 mm by 20 mm ID, eluting with 10% B to 90% B in 3.2 min, hold for 1 min where A=H$_2$O (0.1% trifluoroacetic acid) and B=CH$_3$CN (0.1% trifluoroacetic acid) pumped at 25 mL/min, to produce benzo[b]thiophene-2-carboxylic acid ((S)-3-methyl-1-{1-[4-(piperidin-4-yloxy)-benzenesulfonyl]-piperidin-4-ylcarbamoyl}-butyl)-amide as a mono-trifluoroacetic acid salt (white powder, 23.0 mg, 28% over 11 steps): MS (ESI) 642 [M+H]$^+$.

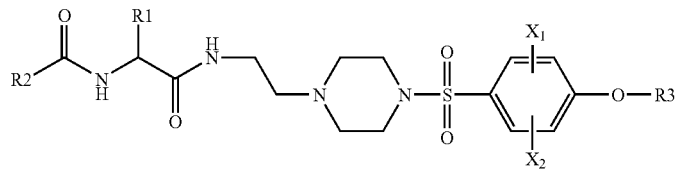

Compounds derived from Scheme 1:

| Example | R1 | R2 | R3 | X1 | X2 | MS (ES+) m/e |
|---|---|---|---|---|---|---|
| 2 | isobutyl | benzothipheneyl | piperidin-4-yl | 3-chloro | H | 676 (M + H) |
| 3 | isobutyl | benzothipheneyl | piperidin-4-yl | 3-bromo | H | 720 (M + H) |
| 4 | isobutyl | benzothipheneyl | piperidin-4-yl | 3-chloro | 5-chloro | 610 (M + H) |
| 5 | isobutyl | benzothipheneyl | pyrrolidin-3(R)-yl | H | H | 628 (M + H) |
| 6 | isobutyl | benzothipheneyl | pyrrolidin-3(R)-yl | 3-chloro | H | 662 (M + H) |
| 7 | isobutyl | benzothipheneyl | pyrrolidin-3(R)-yl | 3-bromo | H | 707 (M + H) |
| 8 | isobutyl | benzothipheneyl | pyrrolidin-3(R)-yl | 3-chloro | 5-chloro | 696 (M + H) |
| 9 | isobutyl | benzothipheneyl | pyrrolidin-3(S)-yl | 3-chloro | H | 662 (M + H) |
| 10 | isobutyl | benzothipheneyl | pyrrolidin-3(S)-yl | 3-bromo | H | 707 (M + H) |

EXAMPLE II

Formulations for pharmaceutical use incorporating compounds of the present invention can be prepared in various forms and with numerous excipients. Examples of such formulations are given below.

| Tablets/Ingredients | Per Tablet |
|---|---|
| 1. Active ingredient (Cpd of Form. I) | 40 mg |
| 2. Corn Starch | 20 mg |
| 3. Alginic acid | 20 mg |
| 4. Sodium Alginate | 20 mg |
| 5. Mg stearate | 1.3 mg |
|  | 2.3 mg |

Procedure for tablets:
Step 1: Blend ingredients No. 1, No. 2, No. 3 and No. 4 in a suitable mixer/blender.
Step 2: Add sufficient water portion-wise to the blend from Step 1 with careful mixing after each addition. Such additions of water and mixing until the mass is of a consistency to permit its conversion to wet granules.
Step 3: The wet mass is converted to granules by passing it through an oscillating granulator using a No. 8 mesh (2.38 mm) screen.
Step 4: The wet granules are then dried in an oven at 140° F. (60° C.) until dry.
Step 5: The dry granules are lubricated with ingredient No. 5.
Step 6: The lubricated granules are compressed on a suitable tablet press.

Inhalant Formulation

A compound of Formula I, (1 mg to 100 mg) is aerosolized from a metered dose inhaler to deliver the desired amount of drug per use.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then sterilized by filtration through a 0.22 micron membrane filter and sealed in sterile containers.

The above specification and Examples fully disclose how to make and use the compounds of the present invention. However, the present invention is not limited to the particular embodiments described hereinabove, but includes all modifications thereof within the scope of the following claims. The various references to journals, patents and other publications which are cited herein comprise the state of the art and are incorporated herein by reference as though fully set forth.

What is claimed is:

1. A compound of Formula (I):

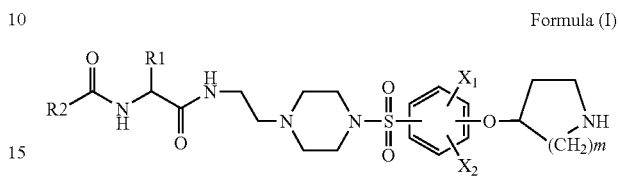

Formula (I)

wherein:
R₁ is isobutyl;
R₂ is benzothiophenyl;
X₁ and X₂ are independently hydrogen, halogen, $C_{1-3}$ alkyl, $C_{1-3}$ alkoxy, nitro, $CF_3$, or CN;
m is 1, or 2;
or a pharmaceutically acceptable salt thereof.

2. A compound of claim 1 wherein X₁ is hydrogen, 3-Bromo, or 3-Chloro; and X₂ is hydrogen or 5-Chloro.

3. A compound of claim 1 selected from the group consisting of:
Benzo[b]thiophene-2-carboxylic acid [(S)-1-(2-{4-[3-chloro-4-(piperidin-4-yloxy)-benzenesulfonyl]-piperazin-1-yl}-ethylcarbamoyl)-3-methyl-butyl]-;
Benzo[b]thiophene-2-carboxylic acid [(S)-1-(2-{4-[3-bromo-4-(piperidin-4-yloxy)-benzenesulfonyl]-piperazin-1-yl}-ethylcarbamoyl)-3-methyl-butyl]-amide;
Benzo[b]thiophene-2-carboxylic acid [(S)-1-(2-{4-[3-chloro-4-((S)-pyrrolidin-3-yloxy)-benzenesulfonyl]-piperazin-1-yl}-ethylcarbamoyl)-3-methyl-butyl]-amide;
Benzo[b]thiophene-2-carboxylic acid [(S)-1-(2-{4-[3-bromo-4-((S)-pyrrolidin-3-yloxy)-benzenesulfonyl]-piperazin-1-yl}-ethylcarbamoyl)-3-methyl-butyl]-amide;
Benzo[b]thiophene-2-carboxylic acid [(S)-3-methyl-1-(2-{4-[4-(piperidin-4-yloxy)-benzenesulfonyl]-piperazin-1-yl}-ethylcarbamoyl)-butyl]-amide; and
Benzo[b]thiophene-2-carboxylic acid [(S)-1-(2-{4-[3,5-dichloro-4-(piperidin-4-yloxy)-benzenesulfonyl]-piperazin-1-yl}-ethylcarbamoyl)-3-methyl-butyl]-amide.

4. A pharmaceutical composition comprising a compound of formula (I) of claim 1 and a pharmaceutically acceptable carrier or excipient.

* * * * *